United States Patent
Bonda

(12) 
(10) Patent No.: US 6,210,658 B1
(45) Date of Patent: Apr. 3, 2001

(54) STABLE SUNSCREEN COMPOSITION CONTAINING A BARIUM COMPOUND, E.G., BARIUM SULFATE, A DIBENZOYLMETHANE DERIVATIVE, E.G., BUTYL METHOXYDIBENZOYLMETHANE (AVOBENZONE), AND A METHOXYCINNAMATE DERIVATIVE, E.G., OCTYL METHOXYCINNAMATE

(75) Inventor: Craig A. Bonda, Wheaton, IL (US)

(73) Assignee: The C. P. Hall Corporation, Chicago, IL (US)

( * ) Notice: Subject to any disclaimer, the term of this patent is extended or adjusted under 35 U.S.C. 154(b) by 0 days.

(21) Appl. No.: 09/592,026

(22) Filed: Jun. 12, 2000

(51) Int. Cl.⁷ .............................. A61K 7/42; A61K 7/44; A61K 7/00
(52) U.S. Cl. ............................. 424/59; 424/60; 424/400; 424/401
(58) Field of Search .............................. 424/59, 60, 400, 424/401

(56) References Cited

U.S. PATENT DOCUMENTS

| | | | |
|---|---|---|---|
| 4,387,089 | 6/1983 | De Polo | 424/59 |
| 4,489,057 | 12/1984 | Welters et al. | 424/47 |
| 4,562,067 | 12/1985 | Hopp et al. | 424/59 |
| 5,783,173 | 7/1998 | Bonda et al. | 424/59 |
| 5,788,954 | 8/1998 | Bonda et al. | 424/59 |
| 5,849,273 | 12/1998 | Bonda et al. | 424/59 |
| 5,993,789 | 11/1999 | Bonda et al. | 424/59 |
| 6,039,935 | 3/2000 | Mohammadi | 424/59 |

OTHER PUBLICATIONS

Sayre, R.M., et al., "Photostability Testing of Avobenzone", Cosmetics & Toiletries magazine, vol. 114, 85–91 (May 1999).

Tarras–Wahlberg, N., et al., "Changes in Ultraviolet Absorption of Sunscreens After Ultraviolet Irradiation", The Journal of Investigative Dermatology, vol. 113, 547–553 (1999).

Turro, N.J., Modern Molecular Photochemistry, Menlo Park, Ca: Benjamin/Cummings (1978) pp. 125–126 and 192–193.

Primary Examiner—Shelley A. Dodson
(74) Attorney, Agent, or Firm—Marshall, O'Toole, Gerstein, Murray & Borun

(57) ABSTRACT

A sunscreen composition containing a UV-A dibenzoylmethane derivative, such as butyl methoxydibenzoylmethane (avobenzone), a UV-B methoxycinnamate derivative, such as ethylhexyl-p-methoxycinnamate (PARSOL MCX), and a barium compound stabilizer for the composition, such as barium sulfate. The barium compound is quite effective in photostabilizing both the dibenzoylmethane derivative UV-A filter compound and the methoxycinnamate UV-B filter compound in the composition.

19 Claims, No Drawings

STABLE SUNSCREEN COMPOSITION CONTAINING A BARIUM COMPOUND, E.G., BARIUM SULFATE, A DIBENZOYLMETHANE DERIVATIVE, E.G., BUTYL METHOXYDIBENZOYLMETHANE (AVOBENZONE), AND A METHOXYCINNAMATE DERIVATIVE, E.G., OCTYL METHOXYCINNAMATE

FIELD OF THE INVENTION

The present invention is directed to a stable sunscreen composition for topical application to human skin to protect the skin against UV radiation damage. More particularly, the present invention is directed to the use of a barium compound, particularly barium sulfate, that is surprisingly effective in stabilizing the combination of a UV-A dibenzoylmethane derivative, particularly butyl methoxydibenzoylmethane, and a methoxycinnamate derivative UV-B sunscreen compound, particularly ethylhexyl-p-methoxycinnamate or octyl methoxycinnamate, such that the sunscreen combination is a more effective sunscreen, having a surprisingly increased sunscreen protection factor (SPF) and such that both the dibenzoylmethane derivative and methoxycinnamate derivative are more effective over a longer period of time so that the sunscreen composition need not be applied to the skin as frequently.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles. Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate (e.g., PARSOL MCX), octyl salicylate; homomenthyl salicylate, and others.

The UV-A filters most commonly used in commercial sunscreen compositions are the dibenzoylmethane derivatives, particularly butyl methoxybenzoylmethane (avobenzone), 4-isopropyl dibenzoylmethane (EUSOLEX 8020), and other dibenzoylmethane derivatives described in U.S. Pat. Nos. 4,489,057; 4,387,089 and 4,562,067, hereby incorporated by reference. It is also well known that some of the UV-A filters, or combinations of UV-A and UV-B filters, suffer in photochemical stability (see R. M. Sayre, J. C. Dowdy, *Photostability Testing of Avobenzone, Cosmetics & Toiletries Magazine* 114, 85–91 (May, 1999); and N. Tarras-Wahlberg et al., *Changes in Ultraviolet Absorption of Sunscreens After Ultraviolet Irradiation*, J. Invest. Derm. 113, 547–553 (1999)). Accordingly, when a UV-B filter, such as 2-ethylhexyl-p-methoxycinnamate (PARSOL MCX), is combined with a dibenzoylmethane derivative UV-A compound, such as PARSOL 1789, the combination becomes less photochemically stable necessitating repeated, frequent coatings over the skin for sufficient UV radiation protection (see Bonda, et al. *The Photochemistry of Sunscreen Photostability*, page 5).

In accordance with the principles of the present invention, it has been found, quite surprisingly, that by including a barium compound, such as barium sulfate, into a sunscreen formulation containing a combination of a UV-A dibenzoylmethane derivative, particularly avobenzone, and a methoxycinnamate derivative UV-B sunscreen agent, such as octyl methoxycinnamate, the sunscreen combination is photochemically stabilized so that the sunscreen composition is more effective for filtering out UV-A and UV-B radiation; the composition filters both UV-A and UV-B radiation for longer periods of time; and, therefore, the sunscreen formulation need not be applied to the skin as frequently while maintaining effective skin protection against UV-A and UV-B radiation.

By the addition of the barium compound, the cosmetic sunscreen formulation can maintain surprisingly effective skin protection against UV radiation both in the UV-A and UV-B range, with or without additional common sunscreen additives, such as benzophenone 3, octocrylene, and/or titanium dioxide. Preferably, the ratio of UV-A to UV-B filter compounds is in the range of about 0.1:1 to about 3:1, preferably about 0.1:1 to about 0.3:1, most preferably about 0.24:1.

SUMMARY OF THE INVENTION

In brief, the present invention is directed to sunscreen compositions containing a dibenzoylmethane derivative UV-A filter compound, such as butyl methoxydibenzoylmethane (avobenzone), together with a UV-B methoxycinnamate derivative, such as octyl methoxycinnamate, and a barium compound stabilizer for the combination of sunscreen agents.

Surprisingly, it has been found the barium compound, particularly barium sulfate, is quite effective in stabilizing the combination of avobenzone and ethylhexyl-p-methoxycinnamate compounds making them more effective; effective for longer periods of time; and, therefore, the sunscreen composition need not be reapplied as frequently to maintain effective UV radiation skin protection.

Accordingly, one aspect of the present invention is to provide a stable sunscreen composition that includes a barium stabilizer compound, particularly barium sulfate, capable of photostabilizing a combination of avobenzone and ethylhexyl-p-methoxycinnamate.

Another aspect of the present invention is to provide a sunscreen composition that includes a barium stabilizer compound for a combination of a dimethylbenzoyl derivative UV-A compound, particularly avobenzone; and a UV-B methoxycinnamate derivative, particularly octyl methoxycinnamate, capable of stabilizing the combination of sunscreen agents, and capable of increasing the sunscreen protection factor (SPF) achievable for the combination of sunscreen agents to an SPF of at least 10, particularly 15–25 SPF.

Another aspect of the present invention is to provide a stable sunscreen composition that has a SPF of at least 15, without a sunscreen composition additive selected from the group consisting of benzophenone 3, octocrylene or other substituted dialkylbenzalmalonates or substituted dialkylmalonates. However, in accordance with the present invention any two additional sunscreen agent(s) can be included with the combination of 2-ethylhexyl-p-methoxycinnamate, avobenzone and the barium compound stabilizer, e.g., barium sulfate.

Still another aspect of the present invention is to provide an improved, stable sunscreen composition containing barium sulfate in an amount of at least about 0.1%, preferably at least about 0.5% by weight, more preferably about 1% to about 3% by weight, that increases the effectiveness of a combination of 2-ethylhexyl-p-methoxycinnamate and avobenzone.

The above and other aspects and advantages of the present invention will become more apparent from the following detailed description of the preferred embodiments.

DETAILED DESCRIPTION OF THE PREFERRED EMBODIMENTS

The sunscreen compositions of the present invention include about 0.1% to about 10% by weight, preferably about 0.5% to about 3% by weight of a barium compound, preferably barium sulfate, to stabilize a combination of a dibenzoylmethane derivative UV-A filter compound, such as butyl methoxybenzoylmethane (avobenzone), included in the sunscreen composition in an amount of about 0.1% to about 6% by weight of the composition, preferably about 0.5% to about 5% by weight, more preferably about 1% to about 3% by weight; and a methoxycinnamate derivative UV-B sunscreen agent, such as ethylhexyl-p-methoxycinnamate (octyl methoxycinnamate), included in the sunscreen composition in an amount of about 0.1% to about 10% by weight of the composition, preferably about 0.5% to about 7.5% by weight, more preferably about 1% to about 5% by weight.

One or more additional sunscreen agents can be added to the combination of ethylhexyl-p-methoxycinnamate, avobenzone, and barium sulfate, e.g., any agent that has at least one chromophoric group absorbing within the ultraviolet range somewhere from 290 to 400 nm, as disclosed in U.S. Pat. No. 6,039,935, hereby incorporated by reference. The additional chromophoric organic sunscreen agents may be divided into the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl, glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naptholsulfonates (sodium salts of 2-naphthol-3,6-disulfonic and of 2-naphthol-6,8-disulfonic acids); dihydroxynaphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy-or-methoxy-substituted benzophenones; uric and vilouric acids; tannic acid and its derivatives; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyldibenzoylmethane).

Particularly useful as additional sunscreen agents are: the diesters and polyesters of naphthalene dicarboxylic acids disclosed in this assignee's U.S. Pat. No. 5,993,789, hereby incorporated by reference, a combination of hexyldecyl benzoate and butyloctyl benzoate, as disclosed in this assignee's U.S. Pat. Nos. 5,783,173; 5,788,954 and 5,849,273, hereby incorporated by reference, butyloctyl salicylate, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid and mixtures thereof.

The combination of UV-A and UV-B sunscreen agents and the barium sulfate stabilizer can be combined with well-known moisturizers, emollients, solvents, lubricants, emulsifiers and other common cosmetic formulation ingredients for emulsification, thickening and to provide other skin enhancement, e.g., moisturizing properties, as well known in the art. The compositions can be produced as lotions, gels, solid sticks, emulsions, aerosols, and all other forms of cosmetic compositions.

The following examples showing the combination of a dibenzoylmethane derivative UV-A sunscreen compound, together with a methoxycinnamate derivative UV-B sunscreen compound, with and without a barium sulfate stabilizer, illustrate the surprising photostabilizing effect of the barium stabilizer compound with the combination of UV-A and UV-B sunscreen agents.

Examples of Barium Compounds as Sunscreen Photostabilizers:

It is well known by those skilled in the art of making sunscreens that the combination of the UV-B filter, ethylhexyl-p-methoxycinnamate, and the UV-A filter, butyl methoxydibenzoylmethane (avobenzone) undergo UV-induced photochemical interactions or reactions that result in the loss of UV absorbance of both sunscreen agents and severely degrade the UV protective capacity of sunscreen compositions containing the combination of sunscreen agents. To illustrate, sunscreen compositions were prepared containing 2% ethylhexyl-p-methoxycinnamate (octyl methoxycinnamate) and 1% butyl methoxydibenzoylmethane (avobenzone), with and without 1.75% barium sulfate, as shown in Table I. Surprisingly, it has been found that adding a barium compound to the same sunscreen composition greatly improves the photostability of both UV filters when used in combination.

TABLE I

Experimental Sunscreen Formulations With And Without Barium Sulfate

| PHASE | CHEMICAL NAME | TRADE NAME | (% w/w) | (% w/w) |
|---|---|---|---|---|
| A | Octyl methoxycinnamate | Parsol MCX | 2.00 | 2.00 |
| A | Hexyldecyl benzoate & Butyloctyl benzoate | HallStar AB | 4.00 | 4.00 |
| A | Isopropyl myristate | Kessco IPM | 7.00 | 7.00 |
| A | Oxybenzone | Escalol 567 | 1.00 | 1.00 |
| A | Avobenzone | Parsol 1789 | 1.00 | 1.00 |
| B | Butyloctyl salicylate | HallBrite BHB | 3.50 | 3.50 |
| B | Barium sulfate | Barium sulfate | 1.75 | 0.00 |
| C | C30–38 Olefin/ | Performa V 1608 | 1.00 | 1.00 |

TABLE I-continued

Experimental Sunscreen Formulations With And Without Barium Sulfate

| PHASE | CHEMICAL NAME | TRADE NAME | (% w/w) | (% w/w) |
|---|---|---|---|---|
|  | Isopropyl maleate/ MA coppolymer |  |  |  |
| C | Stearyl alcohol | Stearyl alcohol | 0.30 | 0.30 |
| C | Polyglyceryl-3 methylglucose distearate | TegoCare 450 | 3.00 | 3.00 |
| D | Deionized water | Water | q.s. | q.s. |
| D | Disodium EDTA | Disodium EDTA | 0.05 | 0.05 |
| D | Butylene glycol | Butylene glycol* | 2.00 | 2.00 |
| D | Glycerin | Glycerin | 4.00 | 4.00 |
| D | Phenoxyethanol()-methylparaben-()ethylparaben-()propylparaben-()butylparaben | Phenonip | 0.70 | 0.70 |
| E | Carbomer | Carbopol Ultrez | 0.20 | 0.20 |
| F | Triethanolamine (99%) | Triethanolamine | 0.20 | 0.20 |

Instructions
1. Blend "A" additives. Heat to 80° C. Stir to dissolve aobenzone and oxybenzone.
2. Increase heat to 90° C. Add "C" additives with stirring until homogeneous.
3. Disperse Barium sulfate in butyloctyl salicylate with stirring. Predisperse carbomer in 50 g water and set aside.
4. Dissolve EDTA salt in water (less 50 g). Heat to 85° C. Preblend preservative, butylene glycol and glycerin and add to water.
5. With homogenization, add oil ("A" + "C") to water ("D"). Add barium sulfate dispersed in butyloctyl salicylate. Add pre-dispersed carbomer ("E"). Maintain heat, homogenize for 10 minutes.
6. Remove from heat. Stir with propeller while cooling.
7. When temperature is below 40° C. slowly add "F". Continue stirring to smooth, homogeneous lotion.

Before exposure to UV radiation, in vitro analysis determined the SPF of the sunscreen composition of Table I, without barium sulfate, to be 21.3. After irradiation with 20 MED (minimum erythemal dose, a standard measure of UV radiation), in vitro analysis determined the SPF of the sunscreen composition without barium sulfate to be 5.6, or only 26% of the sunscreen's original UV protective capacity.

Before exposure to UV radiation, in vitro analysis determined the SPF of the sunscreen composition of Table I, containing barium sulfate, to be 19.4. After irradiation with 20 MED, in vitro analysis determined the SPF to be 14.22, or 78% of the sunscreen's original UV protective capacity. This finding, set forth in more detail in the following Table II, represents a 200% improvement in retention of the sunscreen's original UV protective capacity compared to the non-barium containing sunscreen.

TABLE II

| Formula | Without Barium Compound | | With Barium Compound | |
|---|---|---|---|---|
|  | Pre-UV | Post 20 MED | Pre-UV | Post 20 MED |
| SPF | 21.3 | 5.6 | 19.4 | 15.2 |
| % change |  | −74% |  | −22% |
| Absorbance @ 310 nm | 1.4167 | .76905 | 1.3706 | 1.274 |
| % change |  | −46% |  | −7% |
| Absorbance @ 370 nm | 1.0305 | .41397 | 1.0112 | .77878 |
| % change |  | −60% |  | −23% |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sunscreen composition for topical application to human skin for protection against ultraviolet radiation comprising, in a cosmetically acceptable carrier, at least 0.1% by weight of a barium compound; a least 0.1% by weight of a dibenzoylmethane derivative UV-A filtering compound; and at least 0.1% by weight of a methoxycinnamate derivative UV-B compound.

2. The sunscreen composition of claim 1, wherein the barium compound comprises barium sulfate.

3. The sunscreen composition of claim 2, wherein the dibenzoylmethane derivative comprises butyl methoxydibenzoylmethane.

4. The sunscreen composition of claim 3, wherein the methoxycinnamate derivative comprises ethylhexyl-p-methoxycinnamate.

5. The sunscreen composition of claim 4, wherein the butyl methoxydibenzoylmethane is included in the composition in an amount of 0.1% by weight to about 6% by weight of the composition, and the ethylhexyl-p-methoxycinnamate is included in the composition in an amount of 0.1% by weight to about 10% by weight of the composition.

6. The sunscreen composition of claim 5, wherein the barium sulfate is included in the composition in an amount of 0.1% by weight to about 10% by weight of the composition.

7. The sunscreen composition of claim 6, wherein the butyl methoxydibenzoylmethane is included in the composition in an amount of 0.5% by weight to about 5% by weight of the composition, and the ethylhexyl-p-methoxycinnamate is included in the composition in an amount of 0.5% by weight to about 7.5% by weight of the composition.

8. The sunscreen composition of claim 7, wherein the butyl methoxydibenzoylmethane is included in the composition in an amount of 1.0% by weight to about 3% by weight of the composition, and the ethylhexyl-p-methoxycinnamate is included in the composition in an amount of 1.0% by weight to about 5% by weight of the composition.

9. A composition in accordance with claim 1, wherein said dibenzoylmethane derivative is selected from the group consisting of butyl methoxydibenzoylmethane; 4-(1,1-dimethylethyl)-4'-methoxydibenzoylmethane; 4-isopropyl dibenzoylmethane; and mixtures thereof.

10. A composition in accordance with claim 9, wherein the dibenzoylmethane derivative is butyl methoxydibenzoylmethane.

11. A composition in accordance with claim 10, wherein the dibenzoylmethane derivative is included in the composition in an amount of about 0.5% to about 5% by weight of the composition.

12. A composition in accordance with claim 11, wherein the stabilizing compound is barium sulfate, included in the composition in an amount of about 1% to about 3% by weight of the composition.

13. The composition in accordance with claim 1, wherein the weight ratio of the dibenzoylmethane derivative to methoxycinnamate derivative is in the range of about 0.1:1 to 3:1.

14. The composition in accordance with claim 1, wherein the weight ratio of the dibenzoylmethane derivative to methoxycinnamate derivative is in the range of about 0.1:1 to 0.3:1.

15. A method of filtering out ultraviolet radiation from human skin comprising topically applying to said skin the composition claim 1.

16. A method in accordance with claim 15, wherein said dibenzoylmethane derivative is selected from the group consisting of butyl methoxydibenzoylmethane; 4-(1,1-dimethylethyl)-4'-methoxydibenzoylmethane; 4-isopropyl dibenzoylmethane; and mixtures thereof.

17. A method in accordance with claim 16, wherein the dibenzoylmethane derivative is butyl methoxydibenzoylmethane.

18. A method in accordance with claim 15, wherein the dibenzoylmethane derivative is included in the composition in an amount of about 0.1% to 10% by weight of the composition.

19. A method in accordance with claim 18, wherein the stabilizing compound is barium sulfate.

\* \* \* \* \*